(12) United States Patent
Kim

(10) Patent No.: US 11,684,267 B2
(45) Date of Patent: Jun. 27, 2023

(54) LENS, LIGHT SOURCE DEVICE WITH LENS, AND APPARATUS FOR ESTIMATING CONCENTRATION OF ANALYTE

(71) Applicant: SAMSUNG ELECTRONICS CO., LTD., Suwon-si (KR)

(72) Inventor: Dong Ho Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 363 days.

(21) Appl. No.: 16/841,074

(22) Filed: Apr. 6, 2020

(65) Prior Publication Data

US 2021/0068661 A1 Mar. 11, 2021

(30) Foreign Application Priority Data

Sep. 11, 2019 (KR) .................. 10-2019-0112546

(51) Int. Cl.
| | | |
|---|---|---|
| *G02B 19/00* | (2006.01) | |
| *G02B 3/08* | (2006.01) | |
| *G02B 3/06* | (2006.01) | |
| *A61B 5/00* | (2006.01) | |
| *A61B 5/026* | (2006.01) | |
| *A61B 5/1455* | (2006.01) | |

(52) U.S. Cl.
CPC .......... *A61B 5/0075* (2013.01); *A61B 5/0261* (2013.01); *A61B 5/1455* (2013.01); *G02B 3/08* (2013.01); *G02B 19/0009* (2013.01); *G02B 19/0047* (2013.01); *G02B 3/06* (2013.01)

(58) Field of Classification Search
CPC ............... F21V 5/04; F21V 5/045; F21V 3/02
See application file for complete search history.

(56) References Cited

U.S. PATENT DOCUMENTS

| | | |
|---|---|---|
| 5,222,496 A | 6/1993 | Clarke et al. |
| 5,769,844 A | 6/1998 | Ghaffari |
| 6,692,430 B2 | 2/2004 | Adler |
| 7,251,518 B2 | 7/2007 | Herrmann |
| 7,407,286 B2 | 8/2008 | De Brabander et al. |
| 7,537,368 B2 * | 5/2009 | Mizuyoshi ........... G02B 6/0021 257/E33.059 |

(Continued)

FOREIGN PATENT DOCUMENTS

| | | |
|---|---|---|
| JP | 2009193902 A | 8/2009 |
| JP | 2016-70822 A | 5/2016 |

(Continued)

OTHER PUBLICATIONS

Communication dated Jan. 13, 2021, issued by the European Patent Office in European Application No. 20189661.0.

(Continued)

*Primary Examiner* — William J Carter
(74) *Attorney, Agent, or Firm* — Sughrue Mion, PLLC

(57) ABSTRACT

Provide is a lens which outputs light, emitted by a plurality of light sources, with uniform light distribution. The lens includes a lens body having a first surface which is flat and has an incident hole formed therein, and a second surface which is convex and opposite the first surface; and a plurality of incident surfaces which are recessed from the incident hole toward the second surface, each of the plurality of incident surfaces corresponding to a light source of the plurality of light.

23 Claims, 21 Drawing Sheets

(56) References Cited

U.S. PATENT DOCUMENTS

| 7,548,669 | B2 | 6/2009 | Nakagawa |
| 2007/0070530 | A1* | 3/2007 | Seo .................. G02F 1/133611 |
| | | | 257/E33.059 |
| 2007/0093702 | A1 | 4/2007 | Yu et al. |
| 2014/0378846 | A1 | 12/2014 | Hosoda et al. |
| 2016/0058300 | A1 | 3/2016 | Yoon et al. |
| 2017/0065182 | A1* | 3/2017 | Wang .................. A61B 5/0095 |
| 2019/0099082 | A1 | 4/2019 | Jutte et al. |

FOREIGN PATENT DOCUMENTS

| JP | 2016-101416 A | 6/2016 |
| JP | 6463061 B2 | 1/2019 |
| JP | 6512801 B2 | 5/2019 |
| KR | 10-2009798 B1 | 8/2019 |

OTHER PUBLICATIONS

Communication dated Mar. 17, 2023 by the European Patent Office in European Application No. 20189661.0-1020.

* cited by examiner

FIG. 9
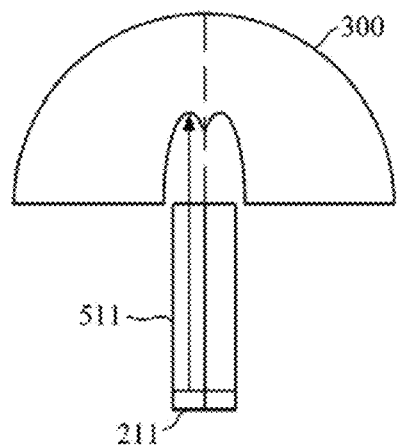
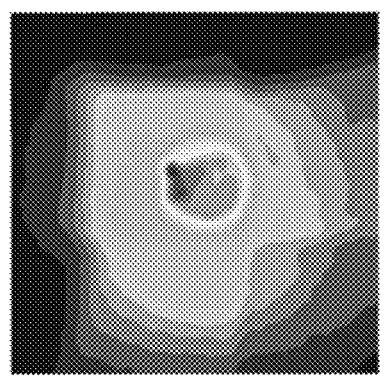
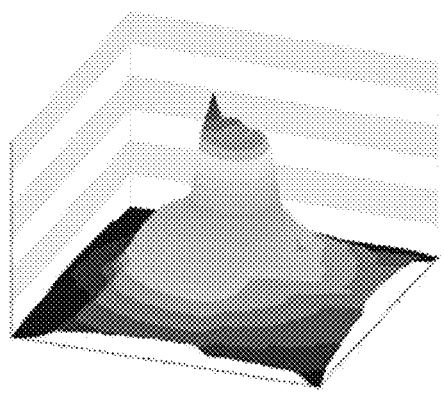

LENS, LIGHT SOURCE DEVICE WITH LENS, AND APPARATUS FOR ESTIMATING CONCENTRATION OF ANALYTE

CROSS-REFERENCE TO RELATED APPLICATION(S)

This application claims priority from Korean Patent Application No. 10-2019-0112546, filed on Sep. 11, 2019, in the Korean Intellectual Property Office, the entire disclosure of which is incorporated herein by reference for all purposes.

BACKGROUND

1. Field

Example embodiments of the disclosure relate to technology for outputting light, emitted from a plurality of light sources, with uniform light distribution.

2. Description of Related Art

Diabetes is a chronic disease that causes various complications and is difficult to cure, such that people with diabetes are advised to check their blood glucose regularly to prevent complications. In particular, when insulin is administered to control blood glucose, the blood glucose level must be closely monitored to avoid hypoglycemia and control insulin dosage. An invasive method of finger pricking is generally used to measure the blood glucose level. However, while the invasive method may provide high reliability in measurement, it may cause pain and inconvenience as well as an increased risk of infection due to the injection. Recently, research has been conducted on a method of non-invasively measuring blood glucose accurately by using a spectrometer without blood sampling.

SUMMARY

Example embodiments provide a lens for outputting light, emitted from a plurality of light sources, with uniform light distribution, a light source device using the lens, and an apparatus for estimating a concentration of an analyte.

According to an aspect of an example embodiment, there is provided a lens configured to output light, emitted by a plurality of light sources, with uniform light distribution, the lens including: a lens body having a first surface which is flat and has an incident hole formed therein, and a second surface which is convex and opposite the first surface; and a plurality of incident surfaces which are recessed from the incident hole toward the second surface, each of the plurality of incident surfaces corresponding to a light source of the plurality of light sources.

The lens body may be made of a glass material or a plastic material.

Each of the plurality of incident surfaces may have a same conic constant.

Each of the plurality of incident surfaces may have a prolate elliptical shape.

The conic constant may be a value ranging between −1.0 and −0.2.

An optical axis of each of the plurality of light sources may pass through a vertex of a corresponding incident surface of the plurality of incident surfaces.

According to an aspect of an example embodiment, there is provided a light source device including: a plurality of light sources configured to emit light; a plurality of waveguides, through which light emitted by the plurality of light sources passes; and a lens configured to output light, having passed through the plurality of waveguides, with uniform light distribution, wherein the lens includes: a lens body having a first surface which is flat and has an incident hole formed therein, and second surface which is convex and opposite the first surface; and a plurality of incident surfaces which are recessed from the incident hole toward the second surface, each of the plurality of incident surfaces corresponding to a light source of the plurality of light sources.

The lens body may be made of a glass material or a plastic material.

Each of the plurality of incident surfaces may have a same conic constant.

Each of the plurality of incident surfaces may have a prolate elliptical shape.

The conic constant may be a value ranging between −1.0 and −0.2.

An optical axis of each of the plurality of light sources may pass through a vertex of a corresponding incident surface of the plurality of incident surfaces.

The plurality of waveguides may be optical fiber waveguides.

The plurality of waveguides may be accommodated in the incident hole.

According to an aspect of an example embodiment, there is provided a light source device including: a plurality of light sources configured to emit light; and a lens configured to output light, emitted by the plurality of light sources, with uniform light distribution, wherein the lens includes: a lens body having a first surface which is flat and has an incident hole formed therein, and a second surface which is convex and opposite the first surface; and a plurality of incident surfaces which are recessed from the incident hole toward the second surface, each of the plurality of incident surfaces corresponding to a light source of the plurality of light sources.

The lens body may be made of a glass material or a plastic material.

Each of the plurality of incident surfaces may have a same conic constant.

Each of the plurality of incident surfaces may have a prolate elliptical shape.

The conic constant may be a value ranging between −1.0 and −0.2.

An optical axis of each of the plurality of light sources may pass through a vertex of a corresponding incident surface of the plurality of incident surfaces.

The plurality of light sources may be accommodated in the incident hole.

According to an aspect of an example embodiment, there is provided an apparatus for estimating a concentration of an analyte, the apparatus including: a plurality of light sources configured to emit light; a plurality of waveguides, through which light emitted by the plurality of light sources passes; and a lens configured to output light, having passed through the plurality of waveguides, to an object with uniform light distribution; a photodetector configured to detect light reflected or scattered from the object; and a processor configured to estimate a concentration of an analyte based on the detected light, wherein the lens includes: a lens body having a first surface which is flat and has an incident hole formed therein, and a second surface which is convex and is opposite to the first surface; and a plurality of incident surfaces which are recessed from the incident hole toward the second surface, each of the plurality of incident surfaces corresponding to a light source of the plurality of light sources.

The analyte may be at least one of glucose, triglyceride, urea, uric acid, lactate, protein, cholesterol, or ethanol.

BRIEF DESCRIPTION OF THE DRAWINGS

The above and/or other aspects, features, and advantages of certain example embodiments will be more apparent from the following description taken in conjunction with the accompanying drawings, in which:

FIGS. 9 and 10 are example diagrams illustrating output light distribution for each light source of the light source device 500 of FIG. 5:

DETAILED DESCRIPTION

Figure 1:
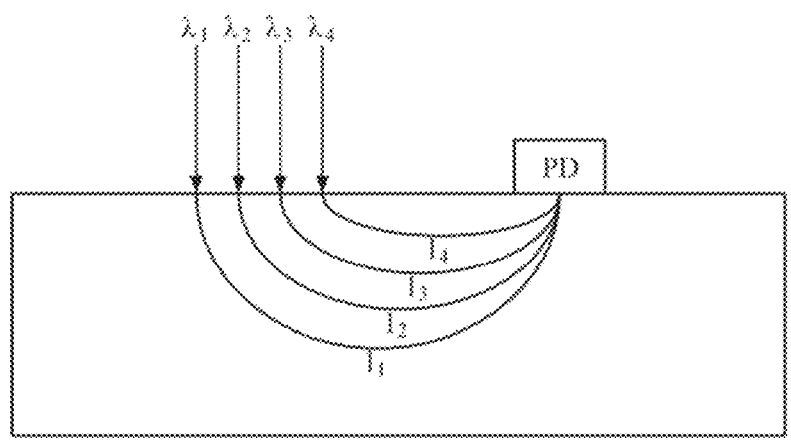
FIG. 1 is a diagram explaining an optical path length when light is emitted at different distances from a photodetector.

Hereinafter, example embodiments will be described in detail with reference to the accompanying drawings. In the following description, a detailed description of known functions and configurations incorporated herein will be omitted when it may obscure the subject matter of the present disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Further, components that will be described in the specification are discriminated merely according to functions mainly performed by the components. That is, two or more components which will be described later can be integrated into a single component. Furthermore, a single component can be separated into two or more components. Moreover, each component can additionally perform some or all of a function executed by another component in addition to the main function thereof. Some or all of the main function of each component can be carried out by another component. Each component may be implemented as hardware, software, or a combination of both.

FIG. 1 is a diagram explaining an optical path length when light is incident on portions at different distances from a photodetector.

As illustrated in FIG. 1, light of a first wavelength $\lambda_1$, which is incident on a first portion positioned at the longest distance from the photodetector PD, travels a first optical path length $l_1$ to be received by the photodetector PD; light of a second wavelength $\lambda_2$, which is incident on a second portion positioned at the second longest distance from the photodetector PD, travels a second optical path length b to be received by the photodetector PD; light of a third wavelength $\lambda_3$, which is incident on a third portion positioned at the third longest distance from the photodetector PD, travels a third optical path length $l_3$ to be received by the photodetector PD; and light of a fourth wavelength $\lambda_4$, which is incident from a fourth portion positioned at the fourth longest distance from the photodetector PD, travels a fourth optical path length $l_4$ to be received by the photodetector PD. The optical path and the optical path length may vary depending on a distance between the light incident portion and the photodetector PD, such that light signals, which are incident on portions at different distances from the photodetector PD and are received by the photodetector PD, may include different information. Accordingly, if an analyte concentration (e.g., blood glucose, etc.) is estimated by using these light signals, the accuracy of estimation may be reduced.

Figure 2:
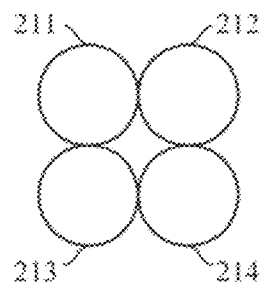
FIG. 2 is an example diagram illustrating an arrangement of a plurality of light sources according to an example embodiment.
Figure 3:
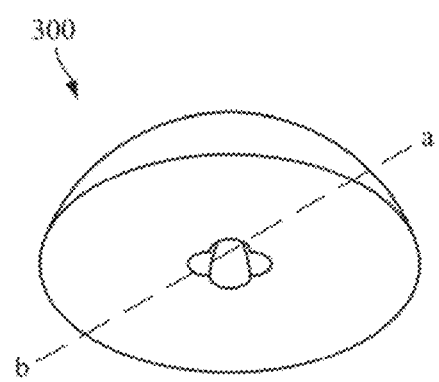
FIG. 3 is a perspective diagram of a lens applied to the plurality of light sources illustrated in FIG. 2.
Figure 4:
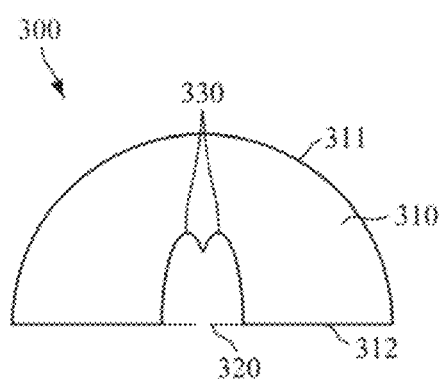
FIG. 4 is a cross-sectional diagram of the lens of FIG. 3, as taken along line a-b thereof, according to an example embodiment.

FIG. 2 is an example diagram illustrating an arrangement of a plurality of light sources according to an example embodiment; FIG. 3 is a perspective diagram of a lens applied to the plurality of light sources illustrated in FIG. 2 according to an example embodiment; and FIG. 4 is a cross-sectional diagram of the lens of FIG. 3, as taken along line a-b thereof, according to an example embodiment. While FIGS. 2, 3, and 4 illustrate four light sources for convenience of explanation, this is merely an example, and the number and arrangement of light sources are not limited thereto.

Referring to FIGS. 2, 3, and 4, in one example embodiment, the plurality of light sources 211, 212, 213, and 214 may be arranged in a square, with each light source being located at the vertices of the square.

Each of the light sources 211, 212, 213, and 214 may emit light of different wavelengths. In one example embodiment, each of the light sources 211, 212, 213, and 214 may emit Near Infrared (NIR) light or Mid Infrared (MIR) light. However, wavelengths of light emitted by each of the light sources 211, 212, 213, and 214 may vary depending on a measurement purpose or types of analyte. Further, each of the light sources 211, 212, 213, and 214 is not necessarily formed of a single light-emitting body, and may be formed of an array of a plurality of light-emitting bodies. If each of the light sources 211, 212, 213, and 214 is formed of a plurality of light-emitting bodies, the plurality of light-emitting bodies may emit light of the same wavelength or light of different wavelengths. In addition, some of the plurality of light-emitting bodies may emit light of the same wavelength, and others may emit light of different wavelengths. In an example embodiment, each of the light sources 211, 212, 213, and 214 may include a light emitting diode (LED), a laser diode, a phosphor, or the like.

The lens 300 may output light, emitted by the light sources 211, 212, 213, and 214, with uniform light distribution. In this case, outputting of light with uniform light distribution may indicate that the output light is distributed with a level of uniformity greater than or equal to a predetermined value.

The lens 300 includes a lens body 310, an incident hole 320, and a plurality of incident surfaces 330.

The lens body 310 may include a top surface 311, which forms an outer shape of a top portion of the lens body 310, and a bottom surface 312 which forms an outer shape of a bottom portion of the lens body 310. The top surface 311 may be a curved surface, i.e., a convex surface, having a curvature which gradually increases from a topmost center towards an edge. The bottom surface 312 may be a flat surface.

In an example embodiment, the lens body 310 may be made of a glass material, such as glass, borosilicate crown glass, or the like, or a plastic material such as polycarbonate, polymethyl methacrylate (PMMA), or the like.

The incident hole 320 is formed on the bottom surface 312, such that light, emitted by the plurality of light sources 211, 212, 213, and 214, may be incident through the incident hole 320.

As illustrated in FIG. 3, the incident hole 320 may be formed in a shape of four overlapping circles or ellipses, the number of which is equal to the number of the light sources. However, the incident hole 320 is not limited thereto, and the incident hole 320 may be formed in various shapes according to the number or arrangement of light sources used in the lens 30).

In an example embodiment, the incident hole 320 may be formed at the center of the bottom surface 312, so that a center point of the incident hole 320 may coincide with a center point of the bottom surface 312.

The incident surface 330 may be recessed from the incident hole 320 toward the interior of the lens 300, i.e., toward the top surface 311.

In an example embodiment, the incident surface 330 may be formed for each of the light sources used in the lens 300. As illustrated herein, four incident surfaces 330 may be formed, the number of which is equal to the number of the light sources 211, 212, 213, and 214.

A surface profile (sag) of each incident surface 330 may be represented by the following Equation 1.

$$Z(s) = \frac{Cs^2}{1 + \sqrt{1 - (1+k)C^2s^2}} \qquad \text{[Equation 1]}$$

Herein, Z(s) denotes the surface profile (sag) of a surface which is parallel to an optical axis; k denotes a conic constant; s denotes a radius of curvature; and C denotes a curvature of 1/s.

The surface profile (sag) relative to the conic constant k is as follows.

| Conic Constant k | Surface Type |
| --- | --- |
| k = 0 | Sphere |
| k = −1 | Parabola |
| k < −1 | Hyperbola |
| −1 < k < 0 | Prolate Ellipse |
| k > 0 | Oblate Ellipse |

In an example embodiment, the incident surfaces 330 have the same conic constant k, which may be a value ranging between −1.0 and −0.2. That is, each incident surface 330 may be formed in a prolate elliptical shape.

As illustrated herein, the incident surfaces 330 may overlap each other, but embodiments are not limited thereto, and the incident surfaces 330 may be formed separately without overlapping each other.

In an example embodiment, an optical axis of each of the plurality of light sources may pass through a vertex of the incident surface 330 which corresponds to each of the plurality of light sources.

Hereinafter, examples of a light source device, to which the lens 300 is applied, will be described with reference to FIGS. 5 to 8.

FIGS. 5, 6, 7, and 8 are diagrams illustrating examples of a light source device, to which the lens 30 is applied. While FIGS. 5, 6, 7, and 8 illustrate an example of applying four light sources, two of the light sources will be omitted for convenience of explanation.

Figure 5:
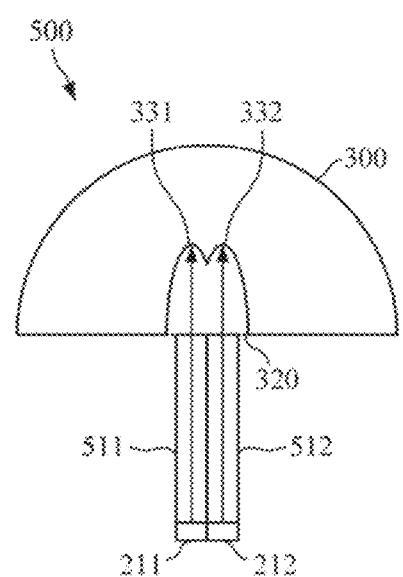
FIGS. 5, 6, 7 and 8 are diagrams illustrating examples of a light source device, to which a lens is applied.

Referring to FIG. 5, the light source device 500 includes a plurality of light sources 211 and 212, a plurality of waveguides 511 and 512, and a lens 300.

The light source 211 may be connected to the waveguide 511, and the light source 212 may be connected to the waveguide 512. That is, light emitted by the light sources 211 and 212 may respectively pass through the waveguides 511 and 512, which are connected to the light sources 211 and 212 respectively, to be incident into the incident hole 321 of the lens 300. The light, incident into the incident hole 320, may be incident on the incident surfaces 311 and 332. Each of the waveguides 511 and 512 includes an optical fiber, and may be disposed outside of the incident hole 320. In this case, a diameter of the incident hole 320 may be greater than a diameter of a bundle of the waveguides 511 and 512.

Figure 6:
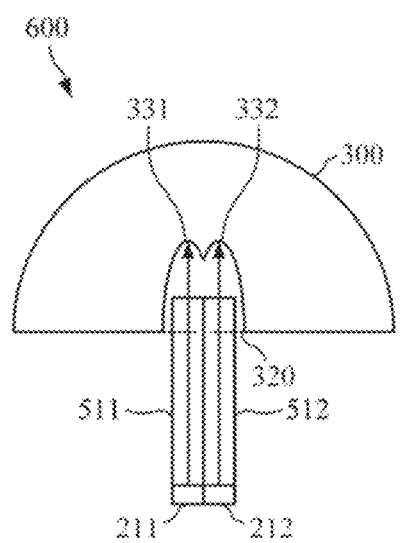

Referring to FIG. 6, a light source device 600 includes the plurality of light sources 211 and 212, the plurality of waveguides 511 and 512, and the lens 300.

The light source 211 may be connected to the waveguide 511, and the light source 212 may be connected to the waveguide 512. That is, light emitted by the light sources 211 and 212 may respectively pass through the waveguides 511 and 512, which are connected to the light sources 211 and 212 respectively, to be incident on the incident surfaces 311 and 332 of the lens 300. Each of the waveguides 511 and 512 includes an optical fiber, and a portion of some or all the waveguides 511 and 512 may be accommodated in the incident hole 320.

Figure 7:
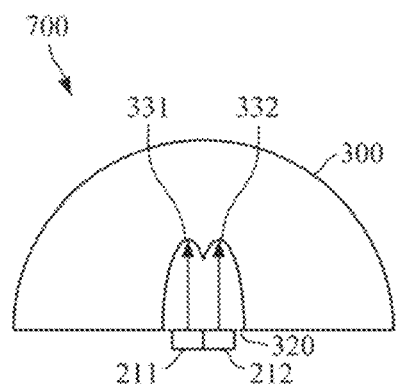

Referring to FIG. 7, a light source device 700 includes the plurality of light sources 211 and 212 and the lens 300.

Unlike the examples of the FIGS. 5 and 6, the light source 70 does not include waveguides such that light, emitted by each of the light sources 211 and 212, may be directly incident into the incident hole 320 of the lens 300. The light, incident into the incident hole 320, may be incident on the incident surfaces 331 and 332. Each of the light sources 211 and 212 may be disposed outside of the incident hole 320. In this case, a diameter of the incident hole 320 may be greater than a diameter of a bundle of the light sources 211 and 212.

Figure 8:
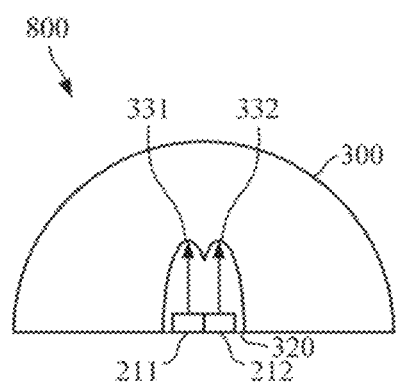

Referring to FIG. 8, a light source device 800 includes the plurality of light sources 211 and 212 and the lens 300. Light, emitted by each of the light sources 211 and 212, may be directly incident on the incident surfaces 311 and 332 of the lens 300. Each of the light sources 211 and 212 may be disposed inside of the incident hole 320.

Figure 10:
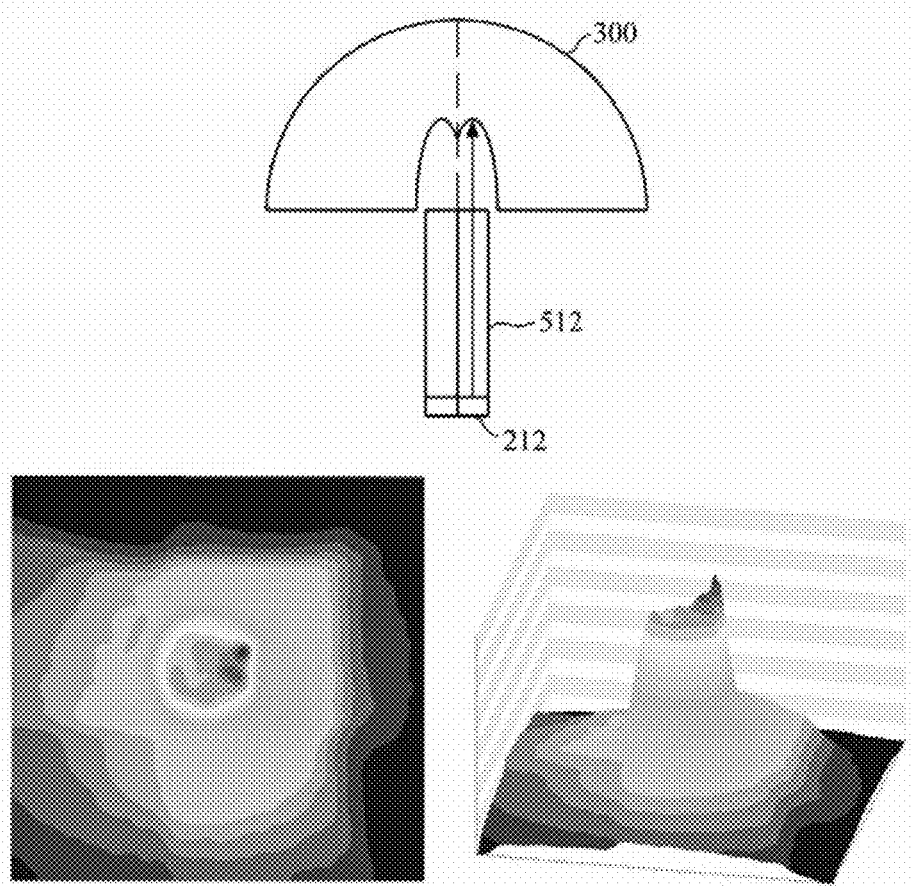

FIGS. 9 and 10 are example diagrams illustrating output light distribution for each light source of the light source device 500 of FIG. 5. More specifically, FIG. 9 is a diagram illustrating output light distribution of the lens 300 when light, emitted by the light source 211, passes through the waveguide 511 to be incident into the lens 300; and FIG. 10 is a diagram illustrating output light distribution of the lens 300 when light, emitted by the light source 212, passes through the waveguide 512 to be incident into the lens 300.

Upon comparison of FIG. 9 with FIG. 10, as illustrated in a lower view thereof, it can be seen that output light distribution in each case is uniform and very similar. Accordingly, even in the case of using a plurality of light sources, light may be emitted uniformly to an object by using the lens 300 according to the example embodiment, thereby reducing a difference in optical path or optical path length depending on a position of light sources or a light incident portion.

Figure 11:
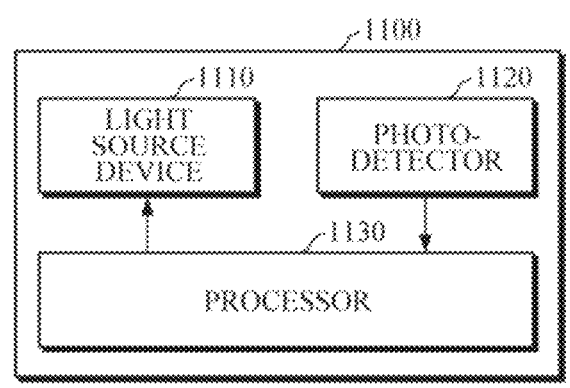
FIG. 11 is a block diagram illustrating a spectrum measuring apparatus according to an example embodiment.

FIG. 11 is a block diagram illustrating a spectrum measuring apparatus according to an example embodiment. The spectrum measuring apparatus 1100 is an apparatus for measuring an in vivo spectrum of an object, and may be included in an electronic device or may be enclosed in a housing to be provided as a separate device. In this case, examples of the electronic device may include a cellular phone, a smartphone, a tablet personal computer (PC), a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is not limited to the above examples.

Referring to FIG. 11, the spectrum measuring apparatus 1100 includes a light source device 1110, a photodetector 1120, and a processor 1130. Here, the light source device 1110 may be any of the light source devices 500, 600, 700, and 800 described above with reference to FIGS. 5 to 10, such that detailed description thereof will be omitted.

The photodetector 1120 may receive a light signal which is reflected or scattered from, or transmitted into, the object. The photodetector 1120 may convert the received light signal into an electric signal, and may transmit the signal to the processor 1130. In an example embodiment, the photodetector 1120 may include a photo diode, a photo transistor (PTr), an image sensor (e.g., charge-coupled device (CCD), complementary metal-oxide semiconductor (CMOS), etc.), and the like. The photodetector 1120 is not necessarily a single device, and may be formed of an array of a plurality of devices.

There may be various numbers and arrangements of the light source device and the photodetector, and the number and arrangement thereof may vary according to types and a purpose of use of an analyte, the size and shape of the electronic device in which the spectrum measuring apparatus 1100 is mounted, and the like. In addition, the spectrum measuring apparatus 1100 may further include various optical elements (e.g., filter, mirror, lens, etc.).

The processor 1130 may process various signals and operations related to measuring an in vivo spectrum.

The processor 1130 may drive each light source of the light source device 1110 sequentially or simultaneously according to a predetermined control signal. In this case, the processor 1130 may drive each light source by referring to predetermined light source driving conditions. In this case, the light source driving conditions may include an emission time, a driving sequence, a current intensity, a pulse duration, and the like of each light source.

The processor 1130 may obtain an in vivo spectrum of an object based on the intensity of light received by the photodetector 1120. Here, the in vivo spectrum may be an absorption spectrum, but is not limited thereto, and may be a reflection spectrum or a transmission spectrum. In one example embodiment, the processor 1130 may reconstruct the in vivo spectrum of the object based on the intensity of light received by the photodetector 1120.

Figure 12:
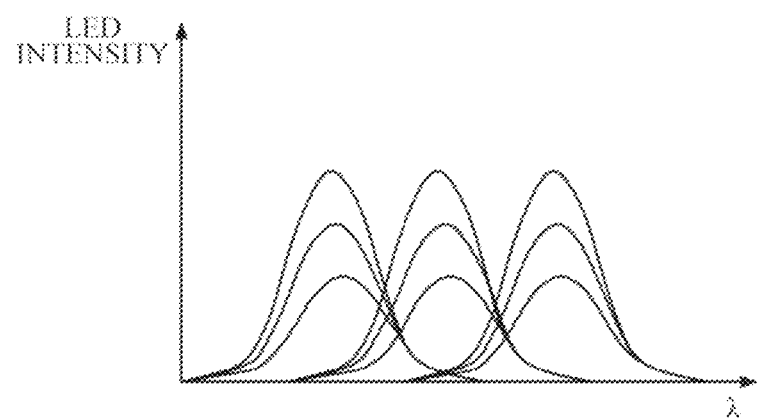
FIGS. 12, 13, and 14 are diagrams explaining an example of reconstructing a spectrum.
Figure 13:
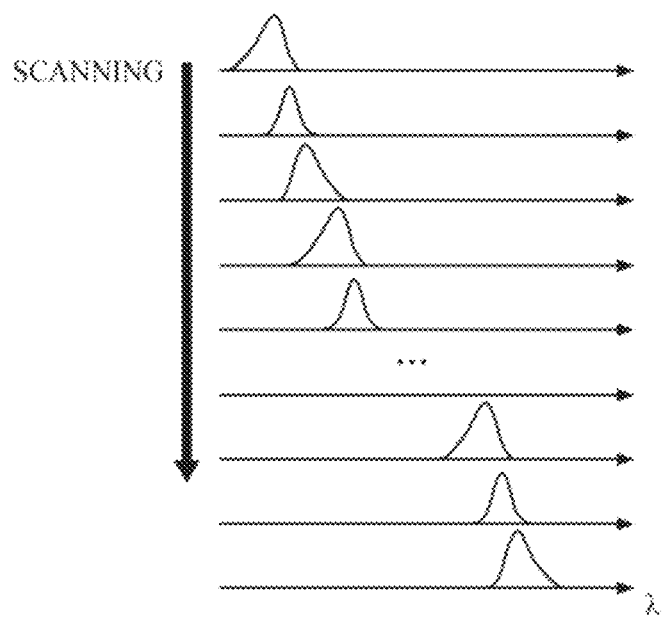
Figure 14:
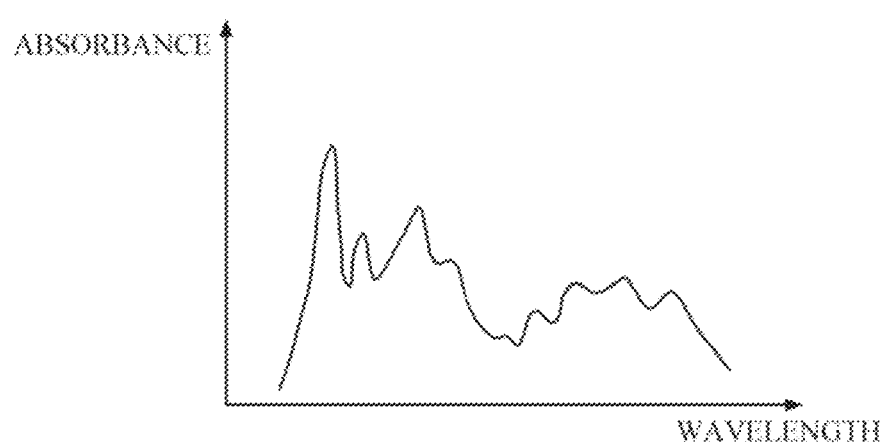

FIGS. 12, 13, and 14 are diagrams explaining an example of reconstructing a spectrum by the processor 1130.

Referring to FIGS. 12, 13, and 14, a light source device is composed of a light source array having N number of light sources; and each light source may be predetermined to have peak wavelengths $\lambda_1, \lambda_2, \lambda_3, \ldots,$ and $\lambda_n$ respectively based on light source driving conditions.

The processor 1130 may sequentially drive each light source of the light source device based on the predetermined light source driving conditions to emit light; and a photodetector may detect light returning from an object. In this case, the processor 1130 may drive only some of the light sources, and may divide the light sources into groups to drive each group of the light sources in a time-division manner.

The processor 1130 may reconstruct a spectrum, as illustrated in FIG. 14, by receiving a light signal from the photodetector. In this case, the processor 1130 may reconstruct the spectrum by using the following Equation 2.

$$y_\alpha = (\alpha E + A^T A)^{-1} A^T p \quad \text{[Equation 2]}$$

Herein, $\alpha$ denotes a parameter for spectrum reconstruction, E denotes a unit matrix, A denotes a light source spectrum measured for each light source, P denotes the intensity of the light signal detected by the photodetector, and $y_\alpha$ denotes the reconstructed spectrum. In this case, the light source spectrum may refer to a spectrum of light emitted by each light source, and information on the light source spectrum may be pre-stored in an internal or external database.

Figure 15:
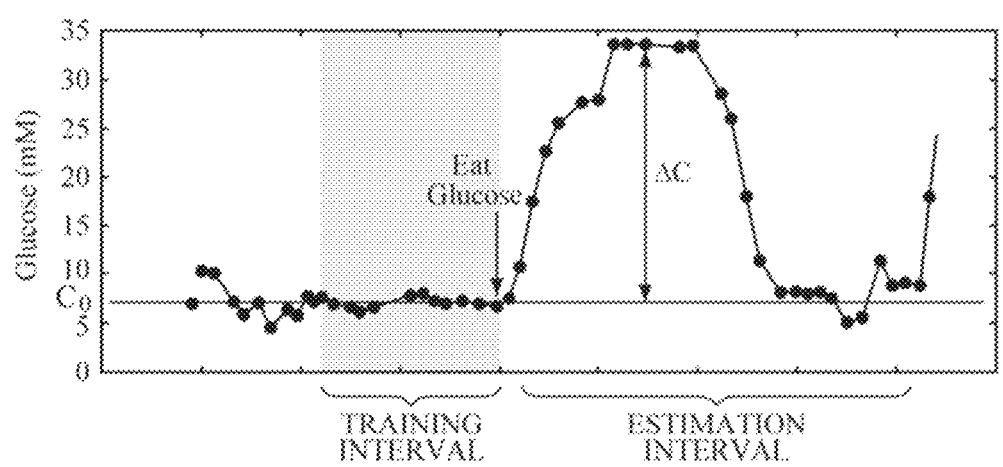
FIGS. 15 and 16 are diagrams explaining a concept of a Net Analyte Signal (NAS) algorithm.
Figure 16:
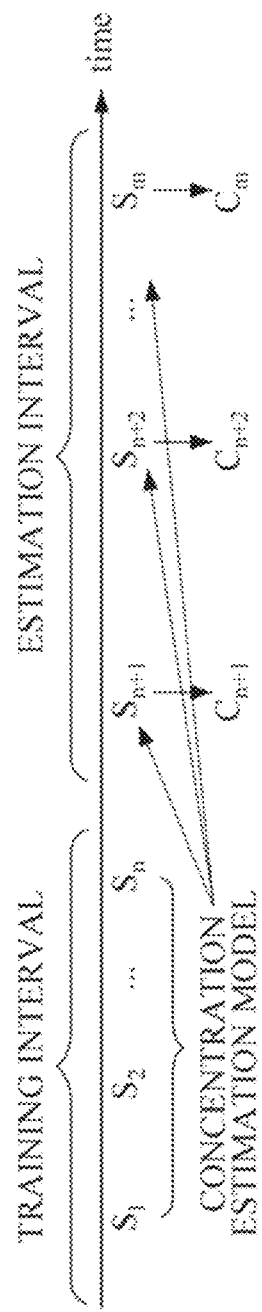

FIGS. 15 and 16 are diagrams explaining a concept of a Net Analyte Signal (NAS) algorithm.

Referring to FIGS. 15 and 16, the Net Analyte Signal (NAS) algorithm may generate an analyte concentration estimation model by learning a spectrum change factor, which is irrelevant to a change in an analyte concentration, using in vivo spectra $S_1, S_2, \ldots,$ and $S_n$ measured in a training interval as training data. Further, the NAS algorithm may estimate analyte concentrations $C_{n+1}, C_{n+2}$ and $C_m$ by using in vivo spectra $S_{n+1}, S_{n+2}, \ldots,$ and $S_m$ measured in an estimation interval after the training interval, and the concentration estimation model generated in the training interval. In this case, the training interval may be an interval (e.g., a fasting interval if an analyte is glucose) in which the concentration of an in vivo analyte does not substantially change.

That is, the NAS algorithm may generate a concentration estimation model based on the in vivo spectra measured in the training interval, and then may estimate an analyte concentration by applying the generated concentration estimation model to the estimation interval.

Figure 17:
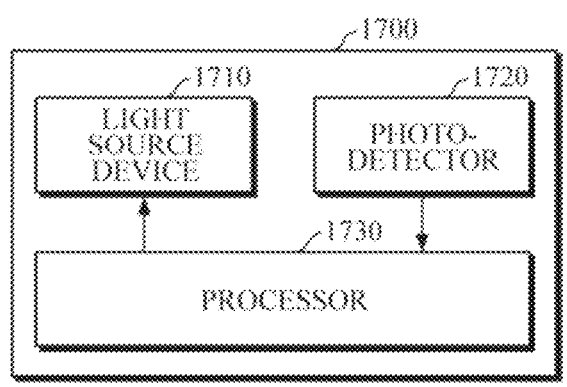
FIG. 17 is a block diagram illustrating an apparatus for estimating an analyte concentration according to an example embodiment.

FIG. 17 is a block diagram illustrating an apparatus for estimating an analyte concentration according to an example embodiment. The apparatus 1700 for estimating an analyte concentration of FIG. 17 is an apparatus for estimating an analyte concentration by analyzing an in vivo spectrum of an object, and may be included in the aforementioned electronic device or may be enclosed in a housing to be provided as a separate device.

Referring to FIG. 17, the apparatus 1700 for estimating an analyte concentration includes a light source device 1710, a photodetector 1720, and a processor 1730. Here, the light source device 1710 and the photodetector 1720 are the same as the light source device 1110 and the photodetector 1120 of FIG. 11, such that detailed description thereof will be omitted.

The processor 1730 may control the overall operation of the apparatus 1700 for estimating an analyte concentration.

By using the light source device 1710 and the photodetector 1720, the processor 1730 may measure a plurality of in vivo spectra in an interval in which an analyte concentration of an object does not substantially change (hereinafter referred to as in vivo training spectrum), and may measure an in vivo spectrum for estimating the analyte concentration of the object (hereinafter referred to as an in vivo estimation spectrum).

The processor 1730 may generate a concentration estimation model based on the measured plurality of in vivo training spectra. In this case, examples of the analyte may include glucose, triglyceride, urea, uric acid, lactate, protein, cholesterol, ethanol, and the like, but the analyte is not limited thereto. In the case where an in vivo analyte is glucose, an analyte concentration may indicate a blood glucose level; and an interval in which an analyte does not substantially change may indicate a fasting interval in which glucose is not introduced into an object. Hereinafter, for convenience of explanation, the following description will be given using glucose as an example of an analyte.

In an example embodiment, the processor 1730 may generate a concentration estimation model by using the NAS algorithm and the plurality of in vivo training spectra measured in the fasting interval. More specifically, the processor 1730 may learn a spectrum change factor, which is irrelevant to a change in the analyte concentration, by using the plurality of in vivo training spectra, measured in the fasting interval, as training data. For example, the processor 1730 may extract a principal component spectrum vector from the plurality of in vivo training spectra, measured in the fasting interval, by using various dimension reduction algorithms such as Principal Component Analysis (PCA), Independent Component Analysis (ICA), Non-negative Matrix Factorization (NMF), Singular Value Decomposition (SVD), and the like. In addition, the processor 1730 may generate the concentration estimation model based on a result of training, i.e., the extracted principal component spectrum vector. In this case, the generated concentration estimation model may be represented by the following Equations 3 and 4.

$$S_m = \sum_i a_i \times S_{pc,i} + \varepsilon_g \times L \times \Delta C \qquad \text{[Equation 3]}$$

$$C_m = \Delta C + C_0 \qquad \text{[Equation 4]}$$

Herein, $C_m$ denotes the analyte concentration, $C_0$ denotes a reference concentration of the analyte (e.g., analyte concentration measured in a in a fasting state), $\Delta C$ denotes a variation in concentration compared to $C_0$, $S_m$ denotes the in vivo estimation spectrum, $S_{pc,i}$ denotes the principal component spectrum, $a_i$ at denotes a contribution of each principal component spectrum to the in vivo estimation spectrum, $\varepsilon_g$ denotes a spectrum of an analyte per unit concentration (e.g., 1 mM) (hereinafter referred to as a pure component spectrum), and L denotes an optical path length, in which $\varepsilon_g$ may be obtained experimentally.

Upon generating the concentration estimation model, and then obtaining the in vivo estimation spectrum for estimating the analyte concentration, the processor 1730 may estimate the analyte concentration by using the in vivo estimation spectrum and the concentration estimation model. For example, the processor 1730 may calculate $\Delta C$ by applying a regression analysis algorithm (e.g., least square method) to Equation 3, and may estimate the analyte concentration by using Equation 4. In the process of calculating $\Delta C$ by applying the regression analysis algorithm, $a_i$ may also be calculated.

Figure 18:
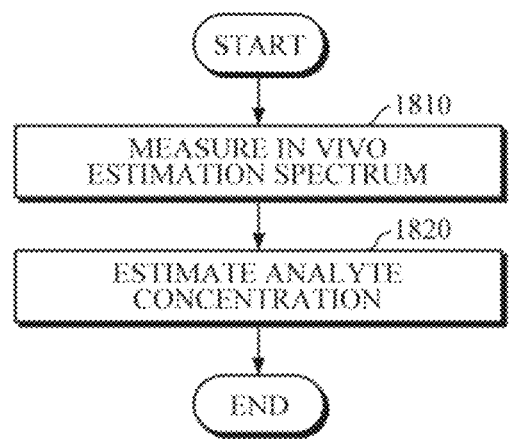
FIG. 18 is a flowchart illustrating an example of a method of estimating an analyte concentration.

FIG. 18 is a flowchart illustrating a method of estimating an analyte concentration according to an example embodiment. The method of estimating an analyte concentration of FIG. 18 may be performed by the apparatus 1700 for estimating an analyte concentration of FIG. 17.

Referring to FIG. 18, the apparatus for estimating an analyte concentration may measure an in vivo estimation spectrum in operation 1810.

The apparatus for estimating an analyte concentration may estimate the analyte concentration by using the in vivo estimation spectrum and a pre-generated concentration estimation model in operation 1820. For example, the apparatus for estimating an analyte concentration may calculate $\Delta C$ by applying a regression analysis algorithm to Equation 3, and may estimate the analyte concentration by using Equation 4. In the process of calculating $\Delta C$ by applying the regression analysis algorithm, $a_i$ may also be calculated.

Figure 19:
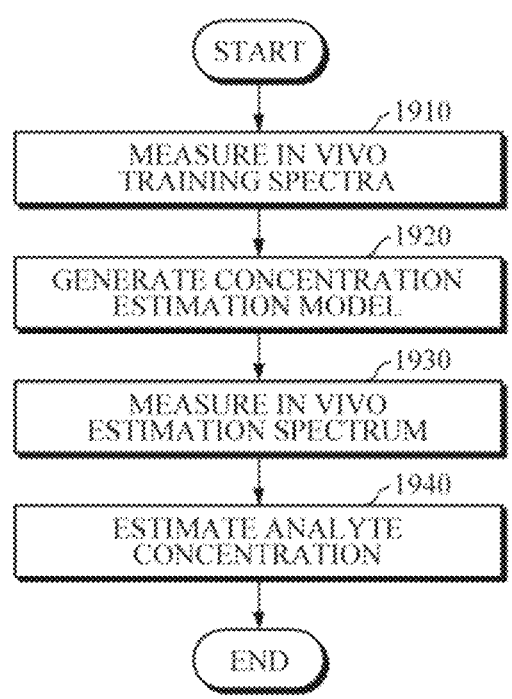
FIG. 19 is a flowchart illustrating another example of a method of estimating an analyte concentration.

FIG. 19 is a flowchart illustrating a method of estimating an analyte concentration according to an example embodiment. The method of estimating an analyte concentration of FIG. 19 may be performed by the apparatus 1700 for estimating an analyte concentration of FIG. 17.

Referring to FIG. 19, the apparatus for estimating an analyte concentration may measure a plurality of in vivo training spectra in operation 1910 in an interval in which an analyte concentration of an object does not substantially change.

The apparatus for estimating an analyte concentration may generate a concentration estimation model based on the measured plurality of in vivo training spectra in operation 1920. In this case, examples of the analyte may include glucose, triglyceride, urea, uric acid, lactate, protein, cholesterol, ethanol, and the like, but the analyte is not limited thereto. In the case where an in vivo analyte is glucose, an analyte concentration may indicate a blood glucose level; and an interval in which an analyte does not substantially change may indicate a fasting interval in which glucose is not introduced into an object.

In one example embodiment, the apparatus for estimating an analyte concentration may generate a concentration estimation model by using the NAS algorithm and the plurality of in vivo training spectra. More specifically, the apparatus for estimating an analyte concentration may learn a spectrum change factor, which is irrelevant to a change in the analyte concentration, by using the plurality of in vivo training spectra as training data. For example, the apparatus for estimating an analyte concentration may extract a principal component spectrum vector from the plurality of in vivo training spectra by using various dimension reduction algorithms. In addition, the apparatus for estimating an analyte concentration may generate the concentration estimation model based on a result of training, i.e., the extracted principal component spectrum vector. In this case, the generated concentration estimation model may be represented by the above Equations 3 and 4.

The apparatus for estimating an analyte concentration may measure an in vivo estimation spectrum in operation 1930, and may estimate the analyte concentration by using the in vivo estimation spectrum and the concentration estimation model in operation 1940.

Figure 20:
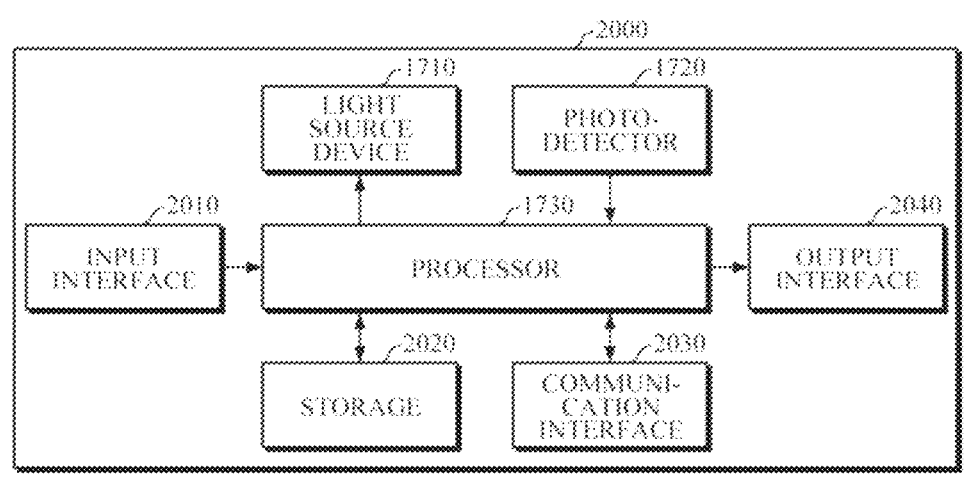
FIG. 20 is a block diagram illustrating another example of an apparatus for estimating an analyte concentration.

FIG. 20 is a block diagram illustrating an apparatus for estimating an analyte concentration according to an example embodiment. The apparatus 2000 for estimating an analyte concentration of FIG. 20 is an apparatus for estimating an analyte concentration by analyzing an in vivo spectrum of an object, and may be included in the aforementioned electronic device or may be enclosed in a housing to be provided as a separate device.

Referring to FIG. 20, the apparatus 2000 for estimating an analyte concentration includes the light source device 1710, the photodetector 1720, the processor 1730, an input interface 2010, a storage 2020, a communication interface 2030, and an output interface 2040. Here, the light source device 1710, the photodetector 1720, and the processor 1730 are described above with reference to FIG. 17, such that detailed description thereof will be omitted.

The input interface 2010 may receive input of various operation signals from a user, in one example embodiment, the input interface 2010 may include one or more of a keypad, a dome switch, a touch pad (static pressure/capacitance), a jog wheel, a jog switch, a hardware (H/W) button, and the like. Particularly, the touch pad, which forms a layer structure with a display, may be referred to a touch screen.

The storage 2020 may be a memory configured to store programs or commands for operation of the apparatus 200 for estimating an analyte concentration, and may store data input to and processed by the apparatus 2000 for estimating an analyte concentration. Further, the storage 2020 may store in vivo spectra, a concentration estimation model, an estimated analyte concentration value, and the like. The storage 2020 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 2000 for estimating an analyte concentration may operate an external storage medium, such as web storage and the like, which performs a storage function of the storage 2020 on the Internet.

The communication interface 2030 may communicate with an external device. For example, the communication interface 2030 may transmit, to the external device, the data input to the apparatus 2000 for estimating an analyte concentration, the data stored in and processed by the apparatus 2000 for estimating an analyte concentration, and the like, or may receive, from the external device, various data useful for estimating an analyte concentration.

In this case, the external device may be medical equipment using the data input to the apparatus 2000 for estimating an analyte concentration, the data stored in and processed by the apparatus 2000 for estimating an analyte concentration, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, or the like, but is not limited thereto.

The communication interface 2030 may communicate with an external device by using one or more of Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WiFi communication, Radio Frequency Identification (RFID) communication, 3G communication, 4G communication, 5G communication, and the like. However, this is merely an example and is not intended to be limiting.

The output interface 2040 may output the data input to the apparatus 2000 for estimating an analyte concentration, the data stored in and processed by the apparatus 2000 for estimating an analyte concentration, and the like. In one example embodiment, the output interface 2040 may output the data input to the apparatus 2000 for estimating an analyte concentration, the data stored in and processed by the apparatus 2000 for estimating an analyte concentration, and the like, by using at least one of an acoustic method, a visual method, and a tactile method. To this end, the output interface 2040 may include a display, a speaker, a vibrator, or the like.

Figure 21:
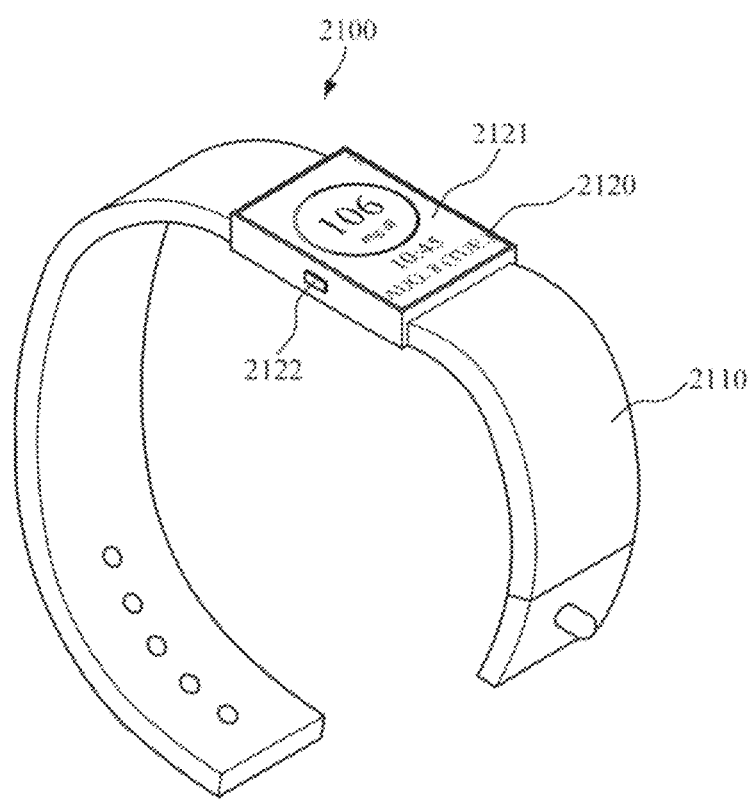
FIG. 21 is a diagram illustrating an example of a wrist-type wearable device.

FIG. 21 is a diagram illustrating an example of a wrist-type wearable device.

Referring to FIG. 21, the wrist-type wearable device 2100 includes a strap 2110 and a main body 2120.

The strap 2110 may be connected to both ends of the main body 2120 so as to be fastened in a detachable manner or may be integrally formed therewith as a smart band. The strap 2110 may be made of a flexible material to be wrapped around a user's wrist so that the main body 2120 may be worn on the wrist.

The main body 2120 may include the aforementioned spectrum measuring apparatus 1100 and/or the aforementioned apparatuses 1700 and 2000 for estimating an analyte concentration. Further, the main body 2120 may include a battery which supplies power to the spectrum measuring apparatus 1100 and the apparatuses 1700 and 2000 for estimating an analyte concentration.

The light source devices 500, 600, 700, and 800 may be provided on the bottom of the main body 2120 to be exposed to a user's wrist. Accordingly, when a user wears the wrist-type wearable device 2100, the light source devices 500, 600, 700, and 80 may naturally come into contact with the user's skin. In this case, the light source devices 500, 600, 700, and 800 may emit light to an object.

The wrist-type wearable device 2100 may further include a display 2121 and an input interface 2122 which are mounted in the main body 2120. The display 2121 may display data processed by the spectrum measuring apparatus 1100, the apparatuses 1700 and 2000 for estimating an analyte concentration, and/or the wrist-type wearable device 2100, processing result data thereof, and the like. The input interface 2122 may receive various operation signals from a user.

The embodiments of the present disclosure can be realized as a computer-readable code stored on a non-transitory computer-readable recording medium and executed by a processor. Codes and code segments needed for realizing embodiments of the present disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

Example embodiments have been described herein. However, it will be apparent to those skilled in the art that various modifications can be made without departing from the inventive concept. Therefore, it is to be understood that that the scope of the present disclosure is not limited to the above-mentioned embodiments, but is intended to include various modifications and equivalents included within the spirit and scope of the appended claims.

What is claimed is:

1. A lens configured to output light, emitted by a plurality of light sources, with uniform light distribution, the lens comprising:
a lens body having a first surface which is flat and has an incident hole formed therein, and a second surface which has a convex shape covering an entire upper surface of the lens body and is opposite the first surface; and
a plurality of incident surfaces which are recessed from the incident hole toward the second surface, each of the plurality of incident surfaces corresponding to a light source of the plurality of light sources,
wherein the incident hole is formed by a plurality of overlapping circules or ellipses, and
wherein a number of the plurality of overlapping circles or ellipses is equal to a number of the plurality of light sources.

2. The lens of claim 1, wherein the lens body is made of a glass material or a plastic material.

3. The lens of claim 1, wherein each of the plurality of incident surfaces has a same conic constant.

4. The lens of claim 3, wherein each of the plurality of incident surfaces has a prolate elliptical shape.

5. The lens of claim 4, wherein the conic constant is a value ranging between −1.0 and −0.2.

6. The lens of claim 1, wherein an optical axis of each of the plurality of light sources passes through a vertex of a corresponding incident surface of the plurality of incident surfaces.

7. A light source device comprising:
a plurality of light sources configured to emit light;
a plurality of waveguides, through which light emitted by the plurality of light sources passes; and
a lens configured to output light, having passed through the plurality of waveguides, with uniform light distribution,
wherein the lens comprises:
a lens body having a first surface which is flat and has an incident hole formed therein, and second surface which has a convex shape covering an entire upper surface of the lens body, and is opposite the first surface; and
a plurality of incident surfaces which are recessed from the incident hole toward the second surface, each of the plurality of incident surfaces corresponding to a light source of the plurality of light sources,
wherein the incident hole is formed by a plurality of overlapping circles or ellipses, and
wherein a number of the plurlity of overlapping circules or ellipses is equal to a number of the plurality of light sources.

8. The light source device of claim 7, wherein the lens body is made of a glass material or a plastic material.

9. The light source device of claim 7, wherein each of the plurality of incident surfaces has a same conic constant.

10. The light source device of claim 9, wherein each of the plurality of incident surfaces has a prolate elliptical shape.

11. The light source device of claim 10, wherein the conic constant is a value ranging between −1.0 and −0.2.

12. The light source device of claim 7, wherein an optical axis of each of the plurality of light sources passes through a vertex of a corresponding incident surface of the plurality of incident surfaces.

13. The light source device of claim 7, wherein the plurality of waveguides are optical fiber waveguides.

14. The light source device of claim 7, wherein the plurality of waveguides are accommodated in the incident hole.

15. A light source device comprising:
a plurality of light sources configured to emit light; and
a lens configured to output light, emitted by the plurality of light sources, with uniform light distribution,
wherein the lens comprises:
a lens body having a first surface which is flat and has an incident hole formed therein, and a second surface which has a convex shape covering an entire upper surface of the lens body and is opposite the first surface; and
a plurality of incident surfaces which are recessed from the incident hole toward the second surface, each of the plurality of incident surfaces corresponding to a light source of the plurality of light sources, wherein the incident hole is formed by a plurality of overlapping circles or ellipses, and wherein a number of the plurality of overlapping circles or ellipses is equal to a number of the plurality of light sources.

16. The light source device of claim 15, wherein the lens body is made of a glass material or a plastic material.

17. The light source device of claim 15, wherein each of the plurality of incident surfaces has a same conic constant.

18. The light source device of claim 17, wherein each of the plurality of incident surfaces has a prolate elliptical shape.

19. The light source device of claim 18, wherein the conic constant is a value ranging between −1.0 and −0.2.

20. The light source device of claim 15, wherein an optical axis of each of the plurality of light sources passes through a vertex of a corresponding incident surface of the plurality of incident surfaces.

21. The light source device of claim 15, wherein the plurality of light sources are accommodated in the incident hole.

22. An apparatus for estimating a concentration of an analyte, the apparatus comprising:

a plurality of light sources configured to emit light;

a plurality of waveguides, through which light emitted by the plurality of light sources passes; and a lens configured to output light, having passed through the plurality of waveguides, to an object with uniform light distribution;

a photodetector configured to detect light reflected or scattered from the object; and a processor configured to estimate a concentration of an analyte based on the detected light, wherein the lens comprises:

a lens body having a first surface which is flat and has an incident hole formed therein, and a second surface which has a convex shape covering an entire upper surface of the lens body and is opposite to the first surface; and a plurality of incident surfaces which are recessed from the incident hole toward the second surface, each of the plurality of incident surfaces corresponding to a light source of the plurality of light sources, wherein the incident hole is formed by a plurality of overlapping circles or ellipses, and wherein a number of the plurality of overlapping circles or ellipses is equal to a number of the plurality of light sources.

23. The apparatus of claim 22, wherein the analyte is at least one of glucose, triglyceride, urea, uric acid, lactate, protein, cholesterol, or ethanol.

* * * * *